United States Patent [19]

Böshagen et al.

[11] 4,349,560
[45] Sep. 14, 1982

[54] ANTIMYCOTIC IMIDAZOLYL-INDENO-THIOPHENE COMPOUNDS, COMPOSITION AND METHOD OF USE

[75] Inventors: Horst Böshagen, Haan; Karl H. Büchel, Burscheid; Wilfried Draber, Wuppertal; Ingo Haller, Wuppertal; Manfred Plempel, Wuppertal, all of Fed. Rep. of Germany

[73] Assignee: Bayer Aktiengesellschaft, Leverkusen, Fed. Rep. of Germany

[21] Appl. No.: 255,068

[22] Filed: Apr. 17, 1982

[30] Foreign Application Priority Data

May 9, 1980 [DE] Fed. Rep. of Germany ....... 3017881

[51] Int. Cl.³ .................. A61K 31/415; C07D 409/04
[52] U.S. Cl. ................................ 424/273 R; 548/336; 549/44; 549/43
[58] Field of Search ..................... 548/336; 424/273 R

[56] References Cited

U.S. PATENT DOCUMENTS

| 3,647,816 | 3/1972 | Draber et al. | 548/336 |
| 3,778,447 | 12/1973 | Draber et al. | 548/336 |
| 4,169,205 | 9/1979 | Hoehn | 548/336 |

Primary Examiner—Henry R. Jiles
Assistant Examiner—N. Harkaway
Attorney, Agent, or Firm—Sprung, Horn, Kramer & Woods

[57] ABSTRACT

The invention relates to imidazolyl-indenothiophene compounds of Formula (I) and a process for their production. Also included in the invention are antimycotic compositions containing said imidazolyl-indenothiophene compounds and methods for the use of said compounds and compositions.

11 Claims, No Drawings

ANTIMYCOTIC IMIDAZOLYL-INDENO-THIOPHENE COMPOUNDS, COMPOSITION AND METHOD OF USE

The present invention relates to certain new imidazolyl-indenothiophene compounds, to a process for their production and their use as antimycotic agents.

It has already been disclosed that imidazolylfluorene derivatives, such as, in particular, 9-(imidazol-1-yl)-9-(2-methylphenyl)-fluorene, in general have good antimycotic properties (see DE-AS (German Published Specification) No. 1,811,654). However, their action is not always completely satisfactory, especially against dermatophytes.

According to the present invention there are provided compounds which are imidazolyl-indeno-thiophenes of the formula

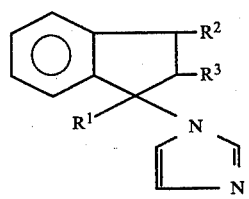
(I)

or a salt thereof, in which
R$^1$ represents an optionally substituted phenyl radical and
R$^2$ and R$^3$, together with the carbon atoms to which they are bonded complete a thiophene ring.

According to the present invention there is further provided a process for the production of a compound of the present invention in which a halogeno-indeno-thiophene of the formula

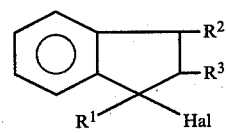
(II)

in which
R$^1$, R$^2$ and R$^3$ have the abovementioned meaning and
Hal represents a chlorine or bromine atom,
is reacted with imidazole in the presence of an acid-binding agent and in the presence of a diluent.

The new imidazolyl-indeno-thiophenes have powerful antimycotic properties. Surprisingly, they exhibit a better, therapeutically useful activity, and in particular in local therapy in the case of dermatophytes, than the imidazolyl-fluorene derivatives known from the state of the art, such as 9-(imidazol-1-yl)-9-(3-methylphenyl)-fluorene, which are closely related compounds chemically and from the point of view of their action. The substances according to the invention thus represent an enrichment of pharmacy.

Particularly preferred compounds of the present invention are those in which R$^1$ represents a phenyl radical which is optionally monosubstituted or polysubstituted (e.g. disubstituted, trisubstituted, etc.) by identical or different substituents (preferably identical substituents) selected from alkyl with 1 to 4 carbon atoms, alkoxy and alkylthio with in each case 1 or 2 carbon atoms, halogen and halogenoalkyl with 1 or 2 carbon atoms and 1 to 5 identical or different halogen atoms (such as fluorine and chlorine atoms), and R$^2$ and R$^3$ preferably have the abovementioned meaning.

Particularly preferred compounds of the present invention are those in which R$^1$ represents a phenyl radical which is optionally monosubstituted or polysubstituted by identical or different substituents selected from fluorine, chlorine, bromine, methyl, ethyl, isopropyl, methoxy, methylthio and trifluoromethyl.

The following compounds of the formulae (Ia), (Ib) and (Ic) may be mentioned specifically, in addition to the compounds mentioned in the preparative Examples, as especially preferred compounds of the present invention:

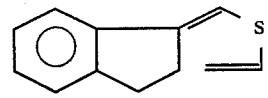
(Ia)

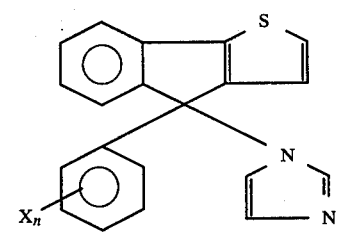
(Ib)

and

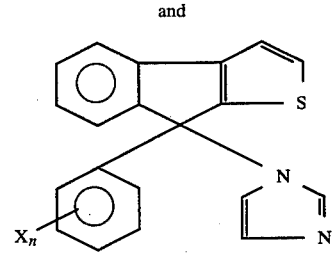
(Ic)

in which X$_n$ has the following meanings;

| X$_n$ | X$_n$ |
| --- | --- |
| — | 4-SCH$_3$ |
| 4-F | 3-CF$_3$ |
| 4-Cl | 2,3-(CH$_3$)$_2$ |
| 4-Br | 2,5-(CH$_3$)$_2$ |
| 3-Cl | 2,4-(CH$_3$)$_2$ |
| 2-Cl | |

If, for example, 4-chloro-4-(2-methylphenyl)-4H-indeno[1,2b]-thiophene and imidazole are used as starting substances, the course of the reaction for the production of compounds according to the present invention is illustrated by the following equation:

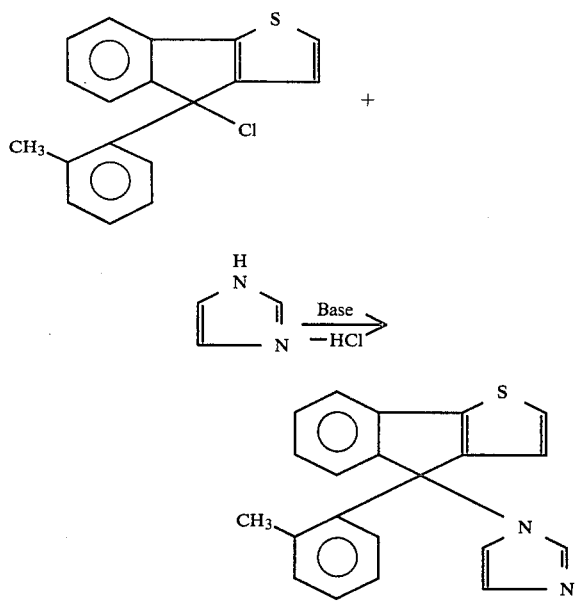

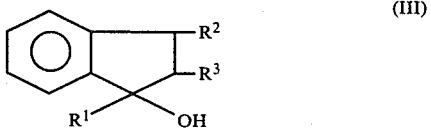

Particularly preferred halogeno-indeno-thiophenes of formula (II) to be used as starting substances are those in which $R^1$, $R^2$ and $R^3$ represent those radicals which have already been mentioned in connection with the description of the preferred and particularly preferred compounds of the present invention.

The halogeno-indeno-thiophenes of the formula (II) are novel. However, they can be obtained in a generally known manner by reacting corresponding hydroxy-indeno-thiophenes of the formula $$\text{(III)}$$

in which $R^1$, $R^2$ and $R^3$ have the abovementioned meaning, with a customary halogenating agent, such as thionyl chloride, thionyl bromide, phosphoryl chloride or phosphoryl bromide, in the presence of an inert organic solvent, such as benzene or toluene, at a temperature between 10° and 100° C. The halogeno-indeno-thiophenes formed, of the formula (II), can be further reacted directly (see also the preparative Examples).

The hydroxy-indeno-thiophenes of the formula (III) are also novel. They are obtained by reacting known thiophene-indenones (see for example J. Org. Chem. 35, 874 and J. Org. Chem. 32, 2441) with an organo-metallic compound, such as, preferably, appropriate phenyl-lithium compounds, in the customary manner in the presence of an inert organic solvent, such as diethyl ether or tetrahydrofuran, at a temperature between 0° and 30° C., and then hydrolysing the product in the customary manner, such as, preferably, with aqueous sulphuric acid.

Preferred possible diluents for the reaction according to the invention are inert polar organic solvents. These include, preferably, nitriles (such as acetonitrile), ketones (such as acetone and methyl ethyl ketone) formamides (such as dimethylformamide), nitromethane and dimethylsulphoxide. The reaction according to the invention is carried out in the presence of an acid-binding agent. Any of the inorganic or organic acid-binding agents which can customarily be used may be added, such as alkali metal carbonates, for example sodium carbonate, potassium carbonate and sodium bicarbonate, or such as tertiary alkylamines, for example triethylamine. An appropriate excess of imidazole is preferably used.

The reaction temperatures can be varied within a substantial range in carrying out the process according to the invention. In general, the reaction is carried out between 20° and 150° C., preferably at 50° to 100° C.

In carrying out the process according to the invention, 1 to 2 moles of imidazole and 1 to 2 moles of acid-binding agent are employed per mole of the compound of the formula (II). The end products of the formula (I) are isolated in the generally customary manner.

The following acids can preferably be used for the preparation of physiologically acceptable acid addition salts of the compounds of the formula (I): hydrogen halide acids (such as hydrobromic acid and, preferably, hydrochloric acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicylic acid, sorbic acid and lactic acid) and sulphonic acids (such as p-toluenesulphonic acid and 1,5-naphthalenedisulphonic acid).

Among the new imidazolyl-indeno-thiophene salts of the invention, those salts that are pharmaceutically acceptable are particularly important and are preferred.

The new free imidazolyl-indeno-thiophenes of the general formula (I) and their salts can be interconverted in any suitable manner; methods for such interconversion are known in the art.

The acid addition salts of the compounds of the formula (I) can be obtained for example by dissolving a compound of the formula (I) in a suitable inert solvent and adding the acid, for example hydrochloric acid, and can be isolated, in a known manner, for example by filtration, and if appropriate purified by washing with an inert organic solvent.

The compounds according to the invention of the formula (I) and their acid addition salts display antimicrobial actions, in particular powerful antimycotic actions. They possess a very broad antimycotic action spectrum, especially against dermatophytes and blastomyces as well as biphase fungi, for example against varieties of Candida, such as *Candida albicans*, varieties of Epidermophyton, such as *Epidermophyton floccosum*, varieties of Aspergillus, such as *Aspergillus niger* and *Aspergillus fumigatus*, varieties of Trichophyton, such as *Trichophyton mentagrophytes*, varieties of Microsporon, such as *Microsporon felineum* and varieties of Penicillium, such as *Penicillium commune*. The listing of these microorganisms in no way implies a limitation of the germs which can be combated but is only illustrative.

Examples which may be mentioned of fields of indication in medicine are: dermatomycoses and systemic mycoses, especially caused by *Trichophyton mentagrophytes* and other varieties of Trichophyton, varieties of Microsporon, *Epidermophyton floccosum*, blastomyces and biphase fungi as well as moulds.

As stated above, the invention also related to the use in medicine of the compounds of the invention.

The present invention provides a pharmaceutical composition containing as active ingredient a compound of the invention in admixture with an inert pharmaceutical carrier, e.g. a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The inert pharmaceutical carriers to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The inert pharmaceutical carriers to be used in pharmaceutical compositions adapted to be formed into suppositories can, for example, be the usual water-soluble diluents, such as polyethylene glycols and fats (e.g. cocoa oil and high esters) e.g. $C_{14}$-alcohol with $C_{16}$-fatty acid)) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5% usually from 0.5 to 95% of the active ingredient by weight of the total composition.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and can be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 2.5 g to 10 g of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably parenterally and, especially intravenously. Preferred pharmaceutical compositions and medicaments are therefore those adapted for administration such as parenterally administration. Administration in the method of the invention is preferably parenteral administration.

In general it has proved advantageous to administer amounts of from 10 mg to 300 mg/kg, preferably 50 mg to 200 mg/kg of body weight per day to achieve effective results. Nevertheless, it can at times be necessary to deviate from those dosage rates, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following Examples 1 to 3 illustrate processes for the production of compounds of the present invention.

EXAMPLE 1

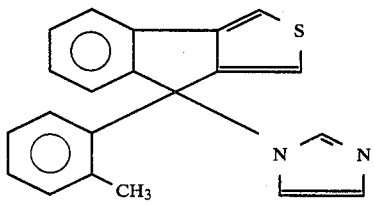
(1)

3.0 g (10 mmoles) of crude 4-chloro-4-(2-methyl-phenyl)-4H-indeno[1,2-c]thiophene were dissolved in 15 ml of acetonitrile, 2.1 g (30 mmoles) of imidazole were added and the mixture was heated under reflux for 5 hours. It was then concentrated in vacuo and 100 ml of 2 N hydrochloric acid were added to the resulting syrupy residue. The hydrochloric acid solution was rendered alkaline with sodium hydroxide solution and extracted with ether. 1.7 g of crude product were obtained from the dried ether extract and were chromatographed over silica gel (mobile phase: chloroform). After recrystallising the product from methanol, 1.1 g (33.5% of theory) of 4-(imidazol-1-yl)-4-(2-methyl-phenyl)-4H-indeno[1,2-c]thiophene of melting point 176° C. were obtained.

Preparation of the precursors

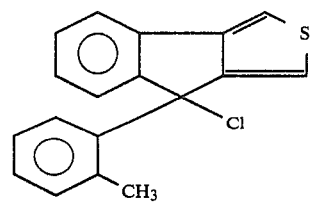

2.8 g (10 mmoles) of 4-hydroxy-4-(2-methyl-phenyl)-4H-indeno[1,2-c]thiophene were dissolved in 20 ml of benzene, and 18 ml of thionyl chloride were added dropwise. The mixture was heated under reflux for 5 hours and then evaporated in vacuo. The resulting syrup was again taken up in 20 ml of benzene and the mixture was again evaporated in vacuo.

3.0 g of crude 4-chloro-4-(2-methyl-phenyl-4H-indeno[1,2-c]thiophene were obtained as a viscous oil, which was further reacted directly.

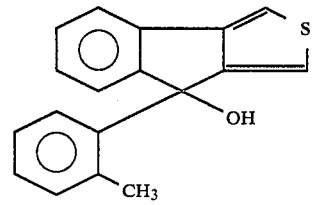

5.0 g (27 mmoles) of 4H-indeno[1,2-c]thiophene-4-one were dissolved in 50 ml of ether/tetrahydrofuran (1:1) and the solution was added dropwise to 200 ml of an ethereal solution of 50 mmoles of 2-methyl-phenyl-lithium. The reaction mixture was stirred at room temperature for 6 hours. 85 ml of 1 N sulphuric acid were then added dropwise, whilst cooling with ice, and the ethereal phase was separated off, dried and evaporated. 13 g of crude product were obtained and were chromatographed over a silica gel column (mobile phase: chloroform). 2.8 g (37.5% of theory) of 4-hydroxy-4-(2-methyl-phenyl)-4H-indeno[1,2-c]thiophene were obtained as a yellowish viscous oil.

EXAMPLE 2

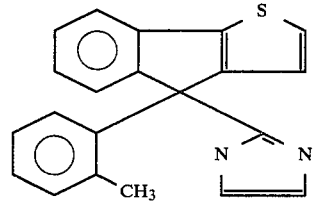
(2)

6.1 g (20 mmoles) of crude 4-chloro-4-(2-methyl-phenyl)-4H-indeno[1,2-b]thiophene were taken up in 30 ml of acetonitrile, 4.1 g (60 mmoles) of imidazole were added and the mixture was heated under reflux for 5 hours. The crude product was then precipitated as a syrup by adding 70 ml of water. The supernatant solution was decanted off and the crude product was taken up in ether. The ether solution was dried and evaporated. The residue was taken up in 100 ml of 2 N hydrochloric acid, the insoluble material was separated off and, after cooling, the base was liberated again with sodium hydroxide solution and extracted with ether. The organic phase was dried over sodium sulphate and concentrated. 4.1 g (62.1% of theory) of 4-(imidazol-1-yl)-4-(2-methyl-phenyl)-4H-indeno[1,2-b]thiophene of melting point 75° C. were obtained.

Preparation of the precursors

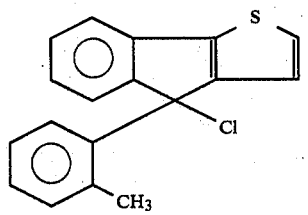

5.6 g (20 mmoles) of 4-hydroxy-4-(2-methyl-phenyl)-4H-indeno[1,2-b]thiophene were dissolved in 40 ml of absolute benzene, and 34 ml of thionyl chloride were added. The mixture was heated under reflux for 5 hours. The reaction solution was then evaporated in vacuo, the oily residue was taken up in cyclohexane, the insoluble material was filtered off and the clear filtrate was evaporated again in vacuo. 6.1 g of crude 4-chloro-4-(2-methyl-phenyl)-4H-indeno[1,2-b]thiophene were obtained as a viscous oil, which was further reacted directly.

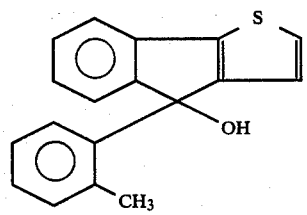

5.0 g (27 mmoles) of 4H-indeno[1,2-b]thiophene-4-one were dissolved in 50 ml of ether and the solution was added dropwise to 50 mmoles of 2-methyl-phenyllithium in 250 ml of absolute ether at room temperature. The reaction solution was subsequently stirred at room temperature for 6 hours and 100 ml of 1 N sulphuric acid were then added. The ether phase was separated off, dried over sodium sulphate and concentrated.

12.3 g of crude product were obtained and were chromatographed over a silica gel column (mobile phase: chloroform). After recrystallising the product from cyclohexane, 4.9 g (65% of theory) of 4-hydroxy-4-(2-methyl-phenyl)-4H-indeno[1,2-b]thiophene of melting point 122° C. were obtained.

EXAMPLE 3

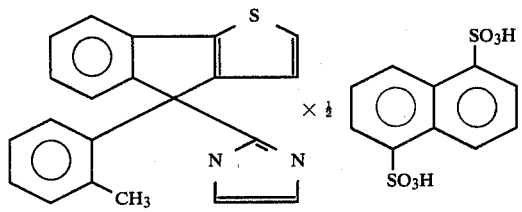

(3)

A virtually quantitative yield of 4-(imidazol-1-yl)-(2-methyl-phenyl)-4H-indeno[1,2-b]thiophene 1,5-naphthalenedisulphonate of melting point 243° C. was obtained by reacting 4-(imidazol-1-yl)-4-(2-methylphenyl)-4H-indeno-[1,2-b]thiophene (obtained as described in Example 2) with 1,5-naphthalenedisulphonic acid.

The following Examples illustrate the in vivo and in vitro activity of compounds of the present invention.

In these Examples, the compounds according to the present invention are each identified by the number (given in brackets) of the corresponding preceding preparative Example.

The known comparison compounds are identified as follows:

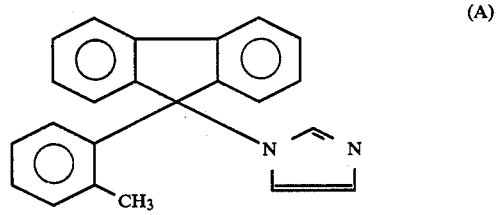

(A)

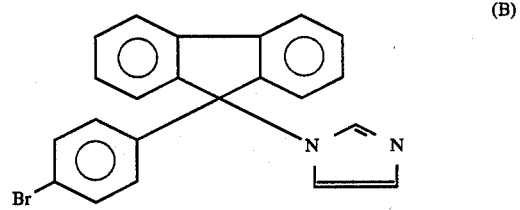

(B)

EXAMPLE A

Antimycotic in vitro activity

Description of the experiment

The in vitro test was carried out as a series dilution test using germ inocula of an average 5×10 germs/ml of substrate. The nutrient medium used was (a) for dermatophytes and moulds: Sabouraud's milieu d'épreuve, and (b) for yeasts: isotonic sensitest broth from Oxoid.

The incubation temperature was 28° C.; the incubation period was 24 hours in the case of yeasts and 96 hours in the case of dermatophytes and moulds.

In this test, compounds (1) and (2) exhibit a better action than the compounds (A) and (B) known from the prior art.

EXAMPLE B

Antimicrobial in vivo activity (local) using the model of experimental trichophytia in guinea pigs Description of the experiment White guinea pigs of the pirbright white strain were infected, on their shaven, non-scarified backs, with a microconidia and macroconidia suspension of *Trichophyton metagrophytes.*

The infected animals were treated locally once daily, starting on the 3rd day after infection, with a 1% strength solution of the preparation according to the invention (in dimethylsulphoxide:glycerol=1:4).

Result

The typical pattern of dermatophytosis with reddening, scaling and loss of hair up to total integumentary defect at the point of infection develops on the untreated animals in the course of 12 days after infection.

Compound (2) shows no signs of infection, whilst reddening, scaling and in some cases also loss of hair occurs with the known compounds (A) and (B).

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to an animal is converted in the patient's body to the active compound.

What is claimed is:

1. A compound which is an imidazolyl-indeno-thiophene of the formula

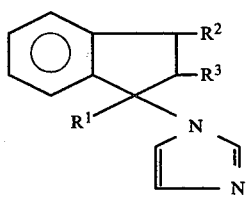 (I)

or a physiologically acceptable acid addition salt thereof, in which $R^1$ represents a phenyl radical which is optionally mono-substituted or polysubstituted by identical or different substituents selected from alkyl with 1 to 4 carbon atoms, alkoxy or alkylthio, in each case with 1 or 2 carbon atoms, halogen or halogenoalkyl with 1 or 2 carbon atoms and with 1 to 5 identical or different halogen atoms which are fluorine or chlorine atoms and $R^2$ and $R^3$, together with the carbon atoms to which they are bonded complete a thiophene ring.

2. A compound according to claim 1 in which $R^1$ represents a phenyl radical which is optionally mono-substituted or polysubstituted by identical or different substituents selected from fluorine, chlorine, bromine, methyl, ethyl, isopropyl, methoxy, methylthio and trifluoromethyl.

3. A compound of claim 1 which is 4-(imidazol-1-yl)-4-(2-methyl-phenyl)-4H-indeno[1,2-c]thiophene.

4. A compound of claim 1 which is 4-(imidazol-1-yl)-4-(2-methyl-phenyl)-4H-indeno[1,2-b]thiophene.

5. A compound of claim 1 which is 4-(imidazol-1-yl)-4-(2-methyl-phenyl)-4H-indeno[1,2-b]thiophene 1,5-naphthalenedisulphonate.

6. An antimycotic pharmaceutical composition containing as an active ingredient an antimycotically effective amount of a compound according to claim 1 in admixture with an inert pharmaceutical carrier.

7. An antimycotic pharmaceutical composition of claim 6 in the form of a sterile or physiologically isotonic aqueous solution.

8. A composition according to claim 6 or 7 containing from 0.5 to 95% by weight of the said active ingredient.

9. A method of combating mycoses in animals in need of said treatment which comprises administering to the animals an antimycotically effective amount of an active compound according to claim 1 either alone or in admixture with an inert pharmaceutical carrier.

10. A method according to claim 9 in which the active compound is administered in an amount of 10 to 300 mg per kg body weight per day.

11. A method according to claim 9 or 10 in which the active compound is administered parenterally.

* * * * *

UNITED STATES PATENT AND TRADEMARK OFFICE
CERTIFICATE OF CORRECTION

PATENT NO. : 4,349,560
DATED : September 14, 1982
INVENTOR(S) : Horst Boshagen et al It is certified that error appears in the above—identified patent and that said Letters Patent is hereby corrected as shown below:

1st pg. "[22] Filed"   Delete "April 17, 1982" and insert
                       --April 17, 1981--

Col. 2, line 20        Delete " 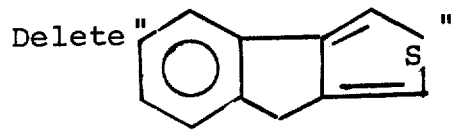 "

and insert--

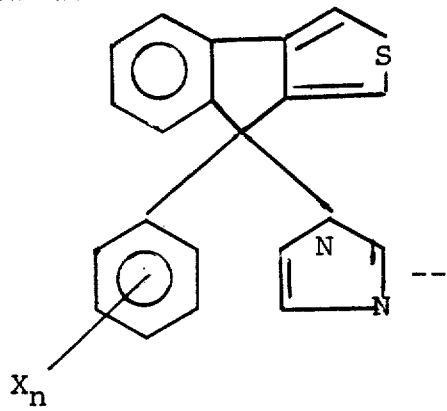

--

Signed and Sealed this

Twenty-first Day of December 1982

[SEAL]

Attest:

GERALD J. MOSSINGHOFF

Attesting Officer        Commissioner of Patents and Trademarks